United States Patent
Arnin

(10) Patent No.: US 10,245,081 B2
(45) Date of Patent: Apr. 2, 2019

(54) RATCHETED SPINAL DEVICE

(75) Inventor: Uri Arnin, Kiryat Tivon (IL)

(73) Assignee: Apifix Ltd., Carmiel (IL)

( * ) Notice: Subject to any disclaimer, the term of this patent is extended or adjusted under 35 U.S.C. 154(b) by 1193 days.

(21) Appl. No.: 13/823,239

(22) PCT Filed: May 5, 2011

(86) PCT No.: PCT/US2011/035278
§ 371 (c)(1),
(2), (4) Date: Mar. 14, 2013

(87) PCT Pub. No.: WO2012/044371
PCT Pub. Date: Apr. 5, 2012

(65) Prior Publication Data
US 2013/0282064 A1 Oct. 24, 2013

Related U.S. Application Data

(60) Provisional application No. 61/344,741, filed on Sep. 27, 2010, provisional application No. 61/457,335, filed on Mar. 3, 2011.

(51) Int. Cl.
*A61B 17/70* (2006.01)
*A61B 17/80* (2006.01)

(52) U.S. Cl.
CPC ...... *A61B 17/7071* (2013.01); *A61B 17/7014* (2013.01); *A61B 17/8009* (2013.01)

(58) Field of Classification Search
CPC ............ A61B 17/8009; A61B 17/7014; A61B 17/7071
See application file for complete search history.

(56) References Cited

U.S. PATENT DOCUMENTS

| | | | | |
|---|---|---|---|---|
| 5,395,371 A | * | 3/1995 | Miller | A61B 17/7007 606/287 |
| 5,700,263 A | | 12/1997 | Schendel | |
| 7,491,221 B2 | * | 2/2009 | David | A61B 17/7007 606/266 |
| 8,439,914 B2 | * | 5/2013 | Ross | A61B 17/62 606/54 |
| 2002/0183755 A1 | * | 12/2002 | Michelson | A61B 17/7059 606/71 |
| 2002/0188296 A1 | | 12/2002 | Michelson | |
| 2003/0114856 A1 | * | 6/2003 | Nathanson | A61B 17/8009 606/70 |

(Continued)

OTHER PUBLICATIONS

PCT Search Report PCT/US2014/016777, dated Jul. 24, 2014.
PCT Search Report PCT/US2011/035278, dated Oct. 28, 2011.

*Primary Examiner* — Julianna N Harvey
(74) *Attorney, Agent, or Firm* — Dekel Patent Ltd; David Klein

(57) ABSTRACT

A ratcheted spinal device including a variable-length member including a ratchet mechanism that has an operative configuration that allows a change in length of the variable-length member in one direction and prevents a change in length of the variable-length member in an opposite direction, wherein the variable-length member includes polyaxial-joint attachment members for attachment to bone, which permit pivoting movement of the attachment members about more than one pivoting axis.

4 Claims, 6 Drawing Sheets

(56) References Cited

U.S. PATENT DOCUMENTS

| | | | | |
|---|---|---|---|---|
| 2004/0249380 A1* | 12/2004 | Glascott | ............. | A61B 17/7032 |
| | | | | 606/278 |
| 2005/0277939 A1* | 12/2005 | Miller, III | ............ | A61B 17/823 |
| | | | | 606/71 |
| 2006/0241591 A1* | 10/2006 | Biscup | ................ | A61B 17/7047 |
| | | | | 606/60 |
| 2009/0093820 A1* | 4/2009 | Trieu | .................. | A61B 17/7004 |
| | | | | 606/103 |
| 2009/0254123 A1* | 10/2009 | Pafford | .............. | A61B 17/7007 |
| | | | | 606/254 |
| 2009/0306717 A1* | 12/2009 | Kercher | ............. | A61B 17/7011 |
| | | | | 606/258 |
| 2010/0004697 A1* | 1/2010 | Fortin | .................... | A61B 17/66 |
| | | | | 606/86 R |
| 2010/0057127 A1 | 3/2010 | McGuire | | |
| 2010/0312243 A1* | 12/2010 | Ross | ...................... | A61B 17/62 |
| | | | | 606/56 |
| 2013/0338713 A1* | 12/2013 | Kawakami | ......... | A61B 17/7014 |
| | | | | 606/258 |

\* cited by examiner

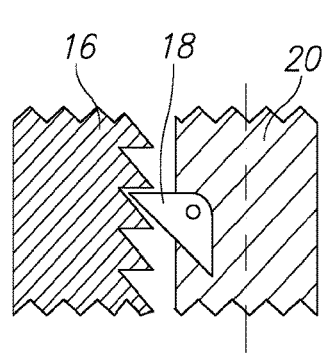 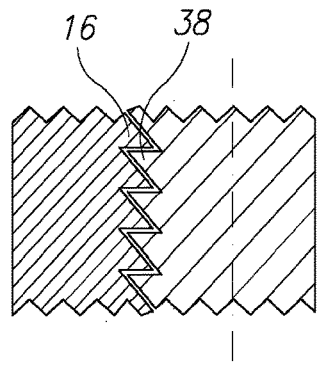
FIG.4A  FIG.4B
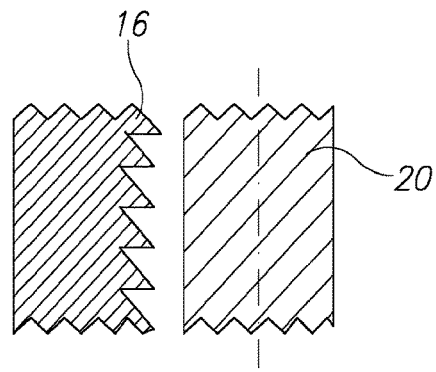
FIG.4C
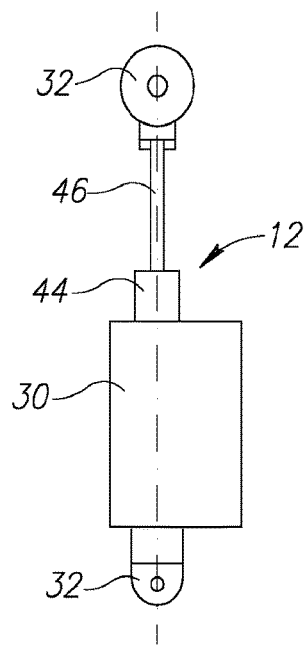
FIG.5

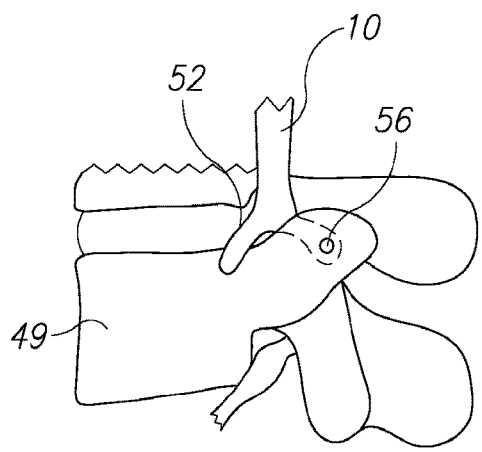 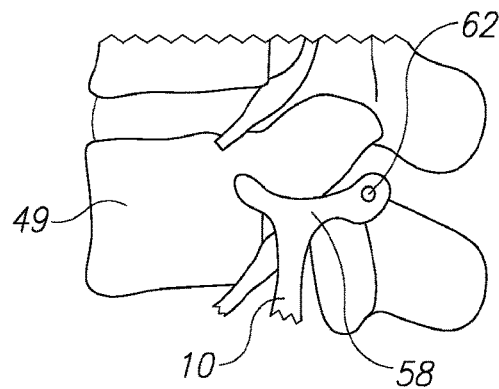
FIG.9A  FIG.9B
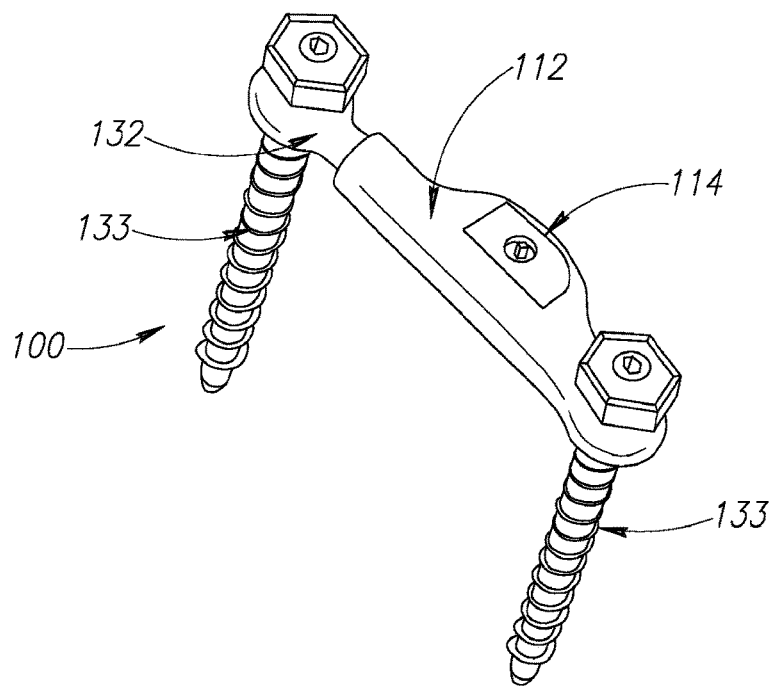
FIG.10

RATCHETED SPINAL DEVICE

FIELD OF THE INVENTION

The present invention relates generally to spinal implants and prostheses, and particularly to a spinal rod having a ratchet mechanism, and also having a locked position and a released position.

BACKGROUND OF THE INVENTION

Scoliosis is a spinal deformity affecting many people. Current surgical treatment involves affixing long fusion rods to the spine by pedicle screws. The rod system is intended to force the deformed spine into a more healthy position.

Unfortunately, there are severe shortcomings to this procedure; the deformation is rarely perfectly corrected, the long fusion for life is not a desired clinical situation and failures are not uncommon

SUMMARY OF THE INVENTION

The present invention seeks to provide an improved ratcheted spinal device that can be lengthened or shortened using a ratchet mechanism. The device has a variable-length member that can be connected to standard pedicle screws as well as to other spinal rods, using appropriate connectors. The variable-length member can also be directly connected to, or be supported by, bony elements of the spine.

In one embodiment of the invention, the device can be set to three different configurations:

a. Ratchet mechanism active and the variable-length member can change in length (extend or contract) in one direction.

b. Ratchet mechanism not active and the variable-length member can move in opposite directions corresponding to the extending and contracting directions.

c. Locked position, wherein the length of the variable-length member is fixed.

In an embodiment of the invention, the selection of these configurations can be done by rotating an internal element of the assembly. For example, the rotation of the internal element can be done using a worm gear mechanism. The worm gear can be activated by a shaft, through a percutaneous procedure or by an implantable mechanism such as an electric motor, magnet arrangement or other means known to those skilled in the art.

In another embodiment of the present invention, the variable-length member can have two portions with different rigidity. For example, the variable-length member can have a flexible portion (e.g., when the ratchet is built such that the rod can be only shortened) like a flexible cable, a rope, a flexible mechanical joint and other means known to those skilled in the art.

In another embodiment of the invention, useful when the rod is supported directly by bone structure of the spine, the hook holding against the bone can have a second hook to fix it to the optimal position.

There is thus provided in accordance with an embodiment of the present invention a ratcheted spinal device including a variable-length member including a ratchet mechanism that has an operative configuration that allows a change in length of the variable-length member in one direction and prevents a change in length of the variable-length member in an opposite direction, wherein the variable-length member includes polyaxial-joint attachment members for attachment to bone, which permit pivoting movement of the attachment members about more than one pivoting axis.

In accordance with an embodiment of the present invention the ratchet mechanism has another operative configuration in which the variable-length member is locked in place, and yet another operative configuration in which the ratchet mechanism is neutralized so that the variable-length member is free to change in length in any of the directions, and a controller controls selection of one of the operative configurations.

In accordance with an embodiment of the present invention the controller selectively moves a pawl of the ratchet mechanism into or out of operative alignment with teeth of the ratchet mechanism, and selectively moves a locking element into and out of locking engagement with the variable-length member. The pawl and locking element may be mounted on a spindle rotated by the controller. Alternatively, the pawl and locking element may be mounted on an eccentric mechanism rotated by the controller.

In accordance with an embodiment of the present invention the polyaxial-joint attachment members are located at or near opposite ends of the variable-length member.

In accordance with an embodiment of the present invention a biasing device is operative to apply an urging force on the variable-length member.

In accordance with an embodiment of the present invention at least one of the polyaxial-joint attachment members includes a ball-and-socket joint. Additionally or alternatively, at least one of the polyaxial-joint attachment members includes a hook.

In accordance with another embodiment of the present invention the ratchet mechanism is toothless.

BRIEF DESCRIPTION OF DRAWINGS

The present invention will be understood and appreciated more fully from the following detailed description, taken in conjunction with the drawings in which:

FIGS. 4A, 4B and 4C are simplified illustrations of three controlled positions of the ratchet mechanism of FIG. 1;

FIG. 5 is a simplified pictorial illustration of a spinal device, constructed and operative in accordance with another embodiment of the invention, designed to be shortened only, having a flexible portion;

FIGS. 7, 8, 9A and 9B are simplified pictorial illustrations of spinal rod support elements placed directly against bony elements of the spine, in accordance with an embodiment of the invention;

FIG. 10 is a simplified illustration of a spinal device, constructed and operative in accordance with another embodiment of the invention, connected to two bone screws;

DETAILED DESCRIPTION OF EMBODIMENTS

Figure 1:
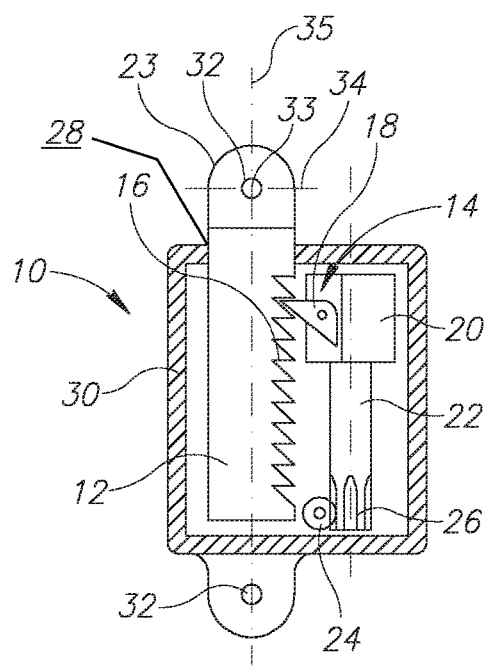
FIG. 1 is a simplified illustration of a longitudinal cross section of the spinal device, constructed and operative in accordance with an embodiment of the invention.

Reference is now made to FIG. 1, which illustrates a ratcheted spinal device 10, constructed and operative in accordance with a non-limiting embodiment of the invention.

The ratcheted spinal device 10 includes a variable-length member 12. In the illustrated embodiment, the variable-length member 12 is a rod. The term "rod" encompasses any slender element of any size and cross-sectional shape, such as but not limited to, a rod, bar, wire and the like.

The ratcheted spinal device 10 includes a ratchet mechanism 14, which has an operative configuration that allows a change in length of the variable-length member 12 in one direction and prevents a change in length of the variable-length member 12 in an opposite direction, as will be explained further below.

In the illustrated embodiment of FIG. 1, ratcheted spinal device 10 includes a ratchet mechanism 14 that has ratchet teeth 16 formed along an axial portion of variable-length member 12, and a pawl 18 arranged to catch on one of the teeth 16. Pawl 18 is mounted on a drum 20 attached to a spindle 22, which is rotated by a controller, which may be a worm gear drive 24 that meshes with gear teeth 26 formed at the end of spindle 22.

Figure 3:
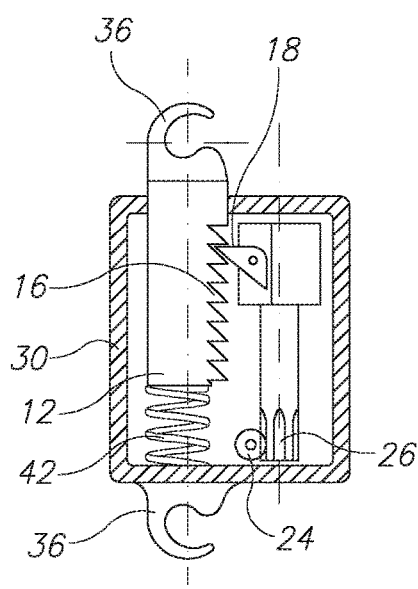
FIG. 3 is another simplified illustration of a longitudinal cross section of the spinal device, including a biasing device, constructed and operative in accordance with another embodiment of the invention.

One end 23 of variable-length member 12 is arranged to linearly move through an aperture 28 formed in a housing 30. Variable-length member 12 includes two polyaxial-joint attachment members 32. In the illustrated embodiment, one polyaxial-joint attachment member 32 is positioned at or near end 23 of variable-length member 12 and another polyaxial-joint attachment member 32 is positioned on housing 30. Alternatively, the variable-length member 12 could be constructed so that the second polyaxial-joint attachment member 32 is mounted on it, at or near an end opposite to end 23. Both polyaxial-joint attachment members 32 are used to attach device 10 to available bone structure of the spine (such as by means of pedicle screws that pass through members 32, as seen in FIG. 10). The polyaxial-joint attachment members 32 permit pivoting movement about more than one pivoting axis, such as about axis 33 (which is perpendicular to the drawing sheet of FIG. 1) and axes 34 and/or 35. In the embodiment of FIG. 1, one or both of polyaxial-joint attachment members 32 have ball-and-socket joints. Additionally or alternatively, as shown in FIG. 3, one or both of polyaxial-joint attachment members 32 include a hook 36.

After installation of device 10 in a patient, in a typical treatment plan, the patient will be asked to bend in a direction that will cause the end 23 of variable-length member 12 to move further out of housing 30 until ratchet teeth 16 click one increment (or more than one increment, if directed by the physician) past pawl 18. This extends the length of variable-length member 12. Pawl 18 holds the variable-length member 12 in place after the incremental length change In this manner, the variable-length member 12 can be lengthened gradually with out causing trauma to the patient.

Alternatively, the ratchet mechanism 14 can be set to allow ratcheted movement of end 23 of variable-length member 12 into housing 30, thereby to shorten the length of variable-length member 12 for each incremental bending of the patient, if the particular treatment plan calls for shortening the length.

Figure 2:
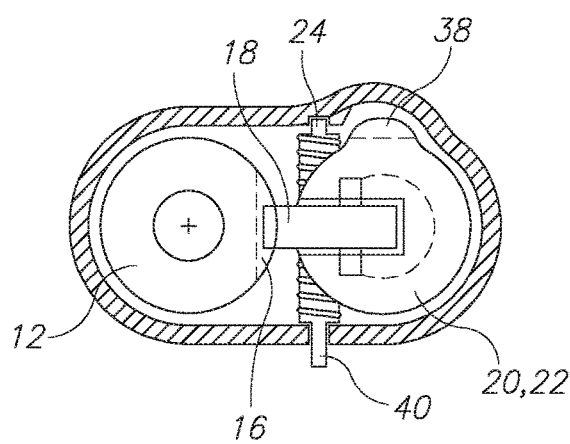
FIG. 2 is a simplified illustration of a cross section perpendicular to that of FIG. 1.

In accordance with an embodiment of the present invention the ratchet mechanism 14 has another operative configuration in which the variable-length member 12 is locked in place. This may be accomplished by means of a locking element 38, which may be positioned on drum 20, as seen in FIG. 2, such as 90° away from pawl 18. The controller (worm gear drive 24) can rotate drum 20/spindle 22 so that pawl 18 is moved away from and out of engagement with ratchet teeth 16, while at the same time locking element 38 (which may be shaped similarly to pawl 18) is moved into locking engagement with one or more of ratchet teeth 16 (seen in FIG. 4B).

In accordance with an embodiment of the present invention the ratchet mechanism 14 has yet another operative configuration in which the ratchet mechanism 14 is neutralized so that variable-length member 12 is free to change in length in any of the directions. This may be accomplished by controller (worm gear drive 24) rotating spindle 22 so both pawl 18 and locking element are moved away from and out of engagement with ratchet teeth 16 (seen in FIG. 4C). The worm gear drive 24 can be activated by a shaft 40, through a percutaneous procedure or by an implantable mechanism such as an electric motor, magnet arrangement or other means known to those skilled in the art.

Reference is now made to FIG. 3. In accordance with an embodiment of the present invention a biasing device 42 is operative to apply an urging force on the variable-length member 12. Biasing device 42 can be a metal spring, plastic spring, an elastomer or gas-actuated extensible rod or shock absorber. The biasing device 42 urges variable-length member 12 to follow the motion direction dictated by ratchet mechanism 14.

Reference is now made to FIG. 5. In this embodiment, the variable-length member 12 includes a rigid portion 44 and a flexible portion 46. Flexible portion 46 may be a cable, rope, plastic wire, flexible mechanical joint or any other means that transfers a pulling force but does not transfer moments from attachment member 32 to rigid portion 44.

Figure 6A:
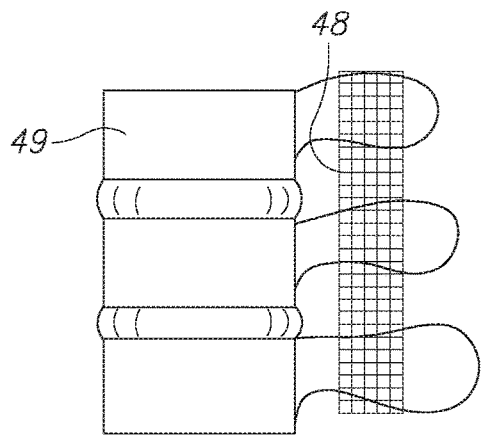
FIGS. 6A and 6B are simplified pictorial illustrations of additional means that can be used together with the device for optimal deformity correction, in accordance with an embodiment of the invention.
Figure 6B:
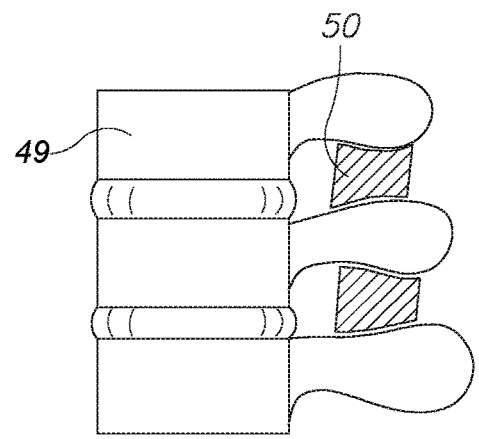

Reference is now made to FIGS. 6A and 6B, which illustrate devices that can be used in conjunction with the device 10 to optimally correct spinal deformity. In FIG. 6A, a flexure-limiting element 48 is deployed around two or more vertebrae 49 to limit the amount of bending or flexion the patient can bend at this portion of the spine. Flexure-limiting element 48 can be a flexible band, wire, string or any other means that prevents the spinous process from flexing too much.

In FIG. 6B, one or more flexure-limiting elements 50 are positioned between two or more vertebrae 48 to limit the amount of bending or flexion the patient can bend at this portion of the spine. Flexure-limiting elements 50 (which may also be used in FIG. 6A) can be made of metal, plastic or any other rigid or semi-rigid material and can have a rectangle, rounded, or elliptical cross section, or any other cross section that fits the anatomy.

Figure 7:
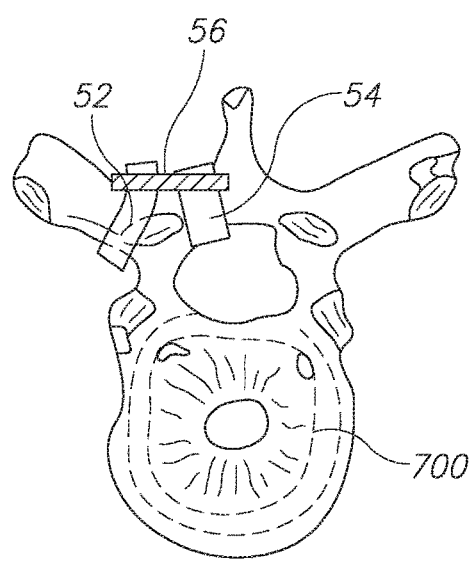

Reference is now made to FIGS. 7 and 9A, which illustrate some supporting elements for supporting or holding the device 10 directly against bony elements of the spine. The supporting elements may be additional, or instead of, the simple hooks illustrated in FIG. 3. The numeral 700 is a top sectional view of the spinal vertebra. A supporting element 52 is firmly connected to the device 10 (not shown here). Supporting element 52 can be located above or under the transverse process. Usually one end of the rod will have a supporting element located above one transverse process and the second end will have a supporting element located under a second transverse process. A hook 54 holds the lamina of the same vertebra and a connecting element 56 fixes supporting element 52 to hook 54. This arrangement enables supporting element 52 to be secured as close as possible to the origin of the transverse process, its strongest point.

Figure 8:
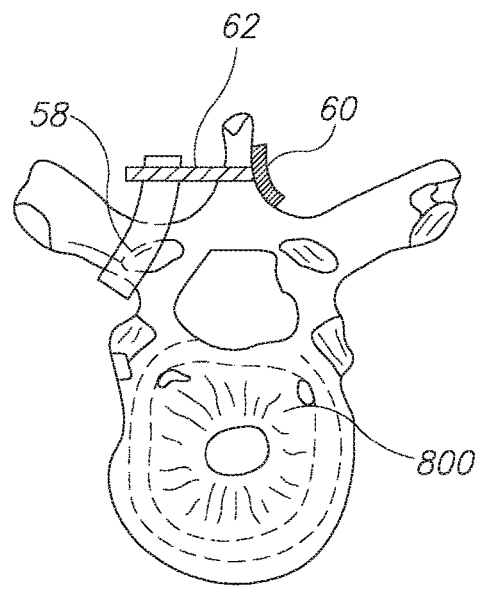
Figure 11:
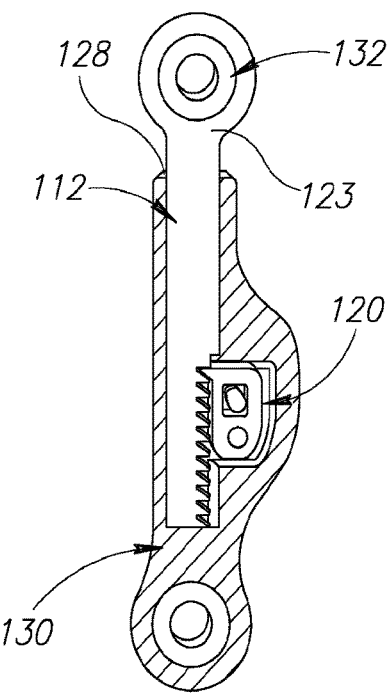
FIG. 11 is a simplified pictorial cross section of the spinal device of FIG. 10.
Figure 12:
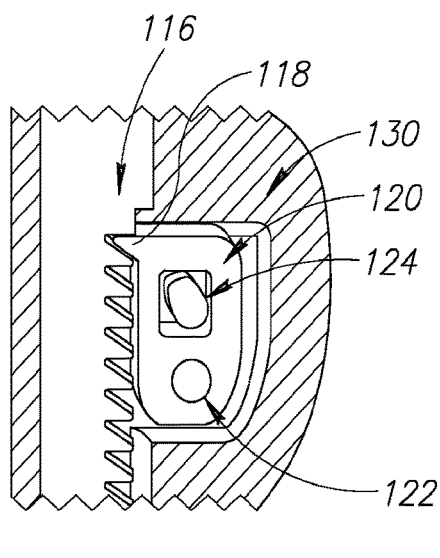
FIG. 12 is a simplified enlarged illustration of the control mechanism of the spinal device of FIG. 10.

Reference is now made to FIGS. 8 and 9B, which illustrate another supporting means when the spinal rod is holding directly against the bony elements of the spine. The numeral 800 is a top sectional view of the spinal vertebra. A supporting element 58 is firmly connected to the device 10 (not shown here). Supporting element 58 can be located above or under the transverse process. Usually one end of the rod will have a supporting element located above one transverse process and the second end will have a supporting element located under a second transverse process. A supporting element 60 is located on the opposite side of the spinous process of the same vertebra and a connecting element 62 fixes supporting element 58 to supporting element 60. This arrangement also enables supporting element 58 to be secured as close as possible to the origin of the transverse process, its strongest point.

Reference is now made to FIGS. 10-13, which illustrates a ratcheted spinal device 100, constructed and operative in accordance with another non-limiting embodiment of the invention.

Similar to the embodiment of FIG. 1, ratcheted spinal device 100 includes a ratchet mechanism 114, which has an operative configuration that allows a change in length of a variable-length member 112 in one direction and prevents a change in length of the variable-length member 112 in an opposite direction. Ratchet mechanism 114 has ratchet teeth 116 formed along an axial portion of variable-length member 112, and a pawl 118 arranged to catch on one of the teeth 116. Pawl 118 extends from a controller element 120 mounted about a pivot 122 and provided with an eccentric cam 124. Rotation of eccentric cam 124 moves pawl 118 to one of three positions: a) in ratchet engagement with teeth 116 so that variable-length member 112 can incrementally move in one direction, b) in locked engagement with teeth 116 so that variable-length member 112 cannot move at all, and c) moved out of engagement with teeth 116 so that variable-length member 112 can move in both directions freely.

Figure 13:
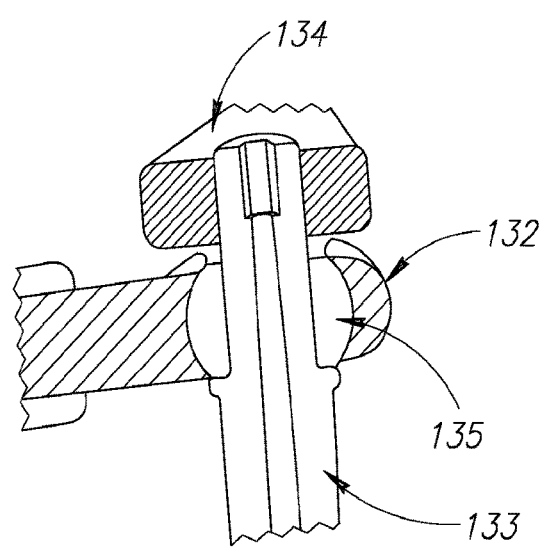
FIG. 13 is a simplified pictorial illustration of an eye joint to connect the device of FIG. 10 to a bone screw.

One end 123 of variable-length member 112 is arranged to linearly move through an aperture 128 formed in a housing 130. Variable-length member 112 includes two polyaxial-joint attachment members 132. As similarly described above, both polyaxial-joint attachment members 132 are used to attach device 100 to available bone structure of the spine, such as by means of pedicle screws 133 that pass through members 132, as seen in FIG. 10. FIG. 13 illustrates a head 135 of pedicle screw 133 passed through polyaxial-joint attachment member 132 (e.g., an eye joint), wherein a nut 134 firmly holds pedicle screw 133 in place while enabling polyaxial rotation.

Figure 14:
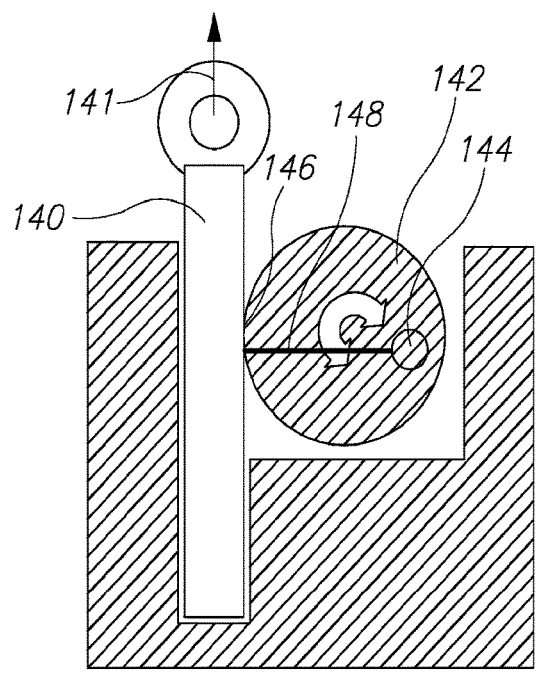
FIGS. 14 and 15 are simplified illustrations of toothless ratchet mechanisms for spinal devices, in accordance with embodiments of the invention.
Figure 15:
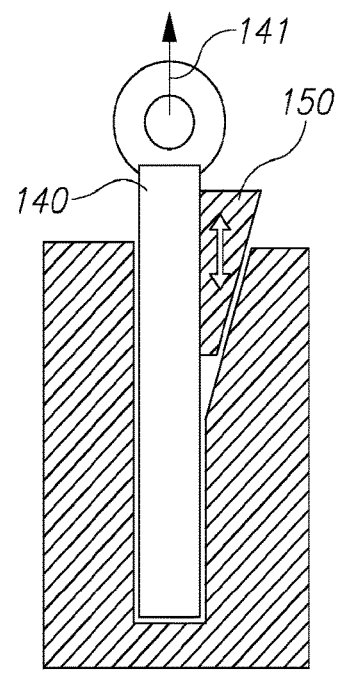

In the above embodiments, the ratchet mechanism has ratchet teeth. In accordance with another embodiment of the present invention the ratchet mechanism is toothless (continuous "ratchet"), which provides infinite positions as opposed to discrete, incremental steps. Two examples are shown in FIGS. 14 and 15. In FIG. 14, a rod 140 is arranged for linear motion in the direction of arrow 141. A disc 142 is eccentrically mounted about a pivot 144. The disc 142 contacts rod 140 at a point 146 above a line 148, which is perpendicular to rod 140 and passes through the center of pivot 144. Rod 140 cannot move downwards (opposite to arrow 141), because it is wedged against disc 142 at point 146.

In FIG. 15, a wedge 150 contacts rod 140. Rod 140 cannot move downwards (opposite to arrow 141), because it is wedged against wedge 150.

Other toothless ratchet mechanism can be use, such as but not limited to, the toothless ratchet and clutch mechanism in U.S. Pat. No. 5,152,197.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A ratcheted spinal device comprising:
a length member disposed in a housing, said length member comprising all portions having a length that protrudes out of said housing a variable amount, said length member and said housing comprising a ratchet mechanism that has an operative configuration that allows a change in the length that said length member protrudes out of said housing in one direction, wherein each of said housing and said length member comprises a polyaxial-joint attachment member for attachment to bone, each of said polyaxial-joint attachment members permitting pivoting movement about more than one pivoting axis, and comprising pedicle screws that pass through said polyaxial-joint attachment members, and wherein for each of said pedicle screws a nut firmly holds said pedicle screw in place while still enabling polyaxial rotation of said pedicle screw even after the nut has been fully tightened, wherein teeth of said ratchet mechanism comprise teeth on said length member which are positioned within said housing such that a change in length of said length member does not necessarily cause the teeth on said length member to protrude out of said housing.

2. The ratcheted spinal device according to claim 1, wherein one of said polyaxial-joint attachment members is located at or near an end of said length member.

3. A ratcheted spinal device comprising:
a length member disposed in a housing, said length member comprising all portions having a length that protrudes out of said housing a variable amount, said length member and said housing comprising a ratchet mechanism that has an operative configuration that allows a change in the length that said length member protrudes out of said housing in one direction, wherein each of said housing and said length member comprises a polyaxial-joint attachment member for attachment to bone, each of said polyaxial-joint attachment members permitting pivoting movement about more than one pivoting axis, and comprising pedicle screws that pass through said polyaxial-joint attachment members, and wherein for each of said pedicle screws a nut firmly holds said pedicle screw in place while still enabling polyaxial rotation of said pedicle screw even after the nut has been fully tightened;

wherein said ratchet mechanism comprises ratchet teeth formed along an axial portion of said length member and a pawl arranged to catch on one of the ratchet teeth, said pawl extending from a controller element mounted about a pivot and provided with an eccentric cam, wherein rotation of said eccentric cam moves said pawl to one of three positions: a) in ratchet engagement with said ratchet teeth so that said length member can incrementally move in one direction, b) in locked engagement with said ratchet teeth so that said length member cannot move at all, and c) moved out of engagement with said ratchet teeth so that said length member can move in both directions freely, and wherein said controller element is mounted in said housing in all of the three positions.

4. A ratcheted spinal device comprising:

a length member disposed in a housing, said length member comprising all portions having a length that protrudes out of said housing a variable amount, said length member and said housing comprising a ratchet mechanism that has an operative configuration that allows a change in the length that said length member protrudes out of said housing in one direction, wherein each of said housing and said length member comprises a polyaxial-joint attachment member for attachment to bone, each of said polyaxial-joint attachment members permitting pivoting movement about more than one pivoting axis, and comprising pedicle screws that pass through said polyaxial-joint attachment members, and wherein for each of said pedicle screws a nut firmly holds said pedicle screw in place while still enabling polyaxial rotation of said pedicle screw even after the nut has been fully tightened, wherein said ratchet mechanism comprises a pawl pivoted about a pivot and said pawl comprises a pawl tooth and a flat-faced portion located on opposing sides of said pivot, and wherein said flat-faced portion is adjacent a flat internal surface of a pawl housing in which said pawl is disposed.

* * * * *